United States Patent
Jin (10) Patent No.: US 10,420,810 B2
(45) Date of Patent: Sep. 24, 2019

(54) TRADITIONAL CHINESE MEDICINE COMPOSITION FOR THE TREATMENT OF DIABETIC RETINOPATHY

(71) Applicant: Ming Jin, Beijing (CN)

(72) Inventor: Ming Jin, Beijing (CN)

(*) Notice: Subject to any disclaimer, the term of this patent is extended or adjusted under 35 U.S.C. 154(b) by 8 days.

(21) Appl. No.: 15/759,052

(22) PCT Filed: Sep. 9, 2016

(86) PCT No.: PCT/CN2016/098510
§ 371 (c)(1),
(2) Date: Mar. 9, 2018

(87) PCT Pub. No.: WO2017/041734
PCT Pub. Date: Mar. 16, 2017

(65) Prior Publication Data
US 2019/0038695 A1    Feb. 7, 2019

(30) Foreign Application Priority Data
Sep. 10, 2015  (CN) .......................... 2015 1 0573355

(51) Int. Cl.
*A61K 36/00*  (2006.01)
*A61K 36/481*  (2006.01)
(Continued)

(52) U.S. Cl.
CPC ............ *A61K 36/481* (2013.01); *A61K 35/62* (2013.01); *A61K 36/232* (2013.01); *A61K 36/258* (2013.01); *A61K 36/28* (2013.01); *A61K 36/284* (2013.01); *A61K 36/36* (2013.01); *A61K 36/537* (2013.01); *A61K 36/54* (2013.01);
(Continued)

(58) Field of Classification Search
CPC ...................................... A61K 36/00
See application file for complete search history.

(56) References Cited

FOREIGN PATENT DOCUMENTS

| CN | 1331994 A | 1/2002 |
|---|---|---|
| CN | 101843802 | 9/2010 |
| CN | 105055785 | 11/2015 |

OTHER PUBLICATIONS

English bibliographic information for CN 1106271 A, 1995.*
(Continued)

*Primary Examiner* — Rosanne Kosson
(74) *Attorney, Agent, or Firm* — Hsuanyeh Law Group PC (57) ABSTRACT

The present invention provides a traditional Chinese medicine (TCM) composition for the treatment of diabetic retinopathy, wherein the active pharmaceutical ingredients (APIs) of the said TCM composition are: *Astragali Radix* 10-80 parts by weight, *Pseudostellariae Radix* 5-30 parts by weight, *Cinnamomi Ramulus* 3-25 parts by weight, *Angelicae Sinensis Radix* 8-60 parts by weight, *Notoginseng Radix* ET *Rhizoma* 2-15 parts by weight, *Dioscoreae Rhizoma* 10-80 parts by weight, *Salviae Miltiorrhizae Radix* ET *Rhizoma* 10-80 parts by weight, *Pheretima* 2-15 parts by weight, *Rehmanniae Radix* 8-60 parts by weight, and *Atractylodis Macrocephalae Rhizoma* 8-60 parts by weight. It has been shown by clinical experiments that, the invented TCM composition has an exact efficacy in patients with macular edema and can effectively improve the patients' visual acuity and visual field and relieve ocular fundus diseases, playing an active role in alleviating macular edema.

8 Claims, 2 Drawing Sheets

(51) Int. Cl.
  *A61K 36/8945*  (2006.01)
  *A61K 35/62*  (2006.01)
  *A61P 27/02*  (2006.01)
  *A61K 36/232*  (2006.01)
  *A61K 36/258*  (2006.01)
  *A61K 36/28*  (2006.01)
  *A61K 36/36*  (2006.01)
  *A61K 36/537*  (2006.01)
  *A61K 36/54*  (2006.01)
  *A61K 36/64*  (2006.01)
  *A61K 36/894*  (2006.01)
  *A61K 36/804*  (2006.01)
  *A61K 36/284*  (2006.01)

(52) U.S. Cl.
  CPC ............ *A61K 36/64* (2013.01); *A61K 36/804* (2013.01); *A61K 36/894* (2013.01); *A61K 36/8945* (2013.01); *A61P 27/02* (2018.01)

(56) References Cited

OTHER PUBLICATIONS

Google Patents English translation of CN 1106271 A, 1995.*
"The Chinese medicinal formulaes for treating diabetes mellitus" published on Oct. 31, 2006, first edition, by "He, Qinghu", "Decoction of Yiqitongmai" pp. 363-364, cited in first office action of Chinese priority application.

* cited by examiner

TRADITIONAL CHINESE MEDICINE COMPOSITION FOR THE TREATMENT OF DIABETIC RETINOPATHY

CROSS-REFERENCE TO RELATED APPLICATIONS

This is the U.S. national stage of International Patent Application No. PCT/CN2016/098510, filed on Sep. 9, 2016, which claims the benefit of priority from Chinese Patent Application No. 201510573355.4, filed on Sep. 10, 2015. The entire contents of both of which are incorporated herein by reference in their entirety for all purposes.

TECHNICAL FIELD

The present invention involves a traditional Chinese medicine composition, specifically, a traditional Chinese medicine composition for the treatment of diabetic retinopathy, belonging to the traditional Chinese medicine field.

BACKGROUND OF THE INVENTION

Diabetes mellitus (DM) is one of the major diseases in the world that pose a serious threat to human health, with a prevalence up to 10% and about 50-60% of DM patients dying of macrovascular and microvascular complications. Diabetic retinopathy (DR) is one of the most important pathological changes in microvascular complications of diabetes, currently ranking top 1 among the causes of blindness and vision disability. How to delay the occurrence and development of DR has now become the focus of attention and research in the medical field. One of the important pathogenesis is microcirculation disturbance. From the perspective of whole-course control of diabetic retinopathy, drugs, laser, surgery and other integrated means are its treatment options. Early diabetic retinopathy is a key part of Chinese medicine intervention, which, especially with macular edema, causes central vision loss, making DM patients more painful than DM itself. Rational use of traditional Chinese medicine can delay the development of diabetic retinopathy and intercept early macular edema, having an advantage in maintaining visual acuity. Although diabetic macular edema has always been a difficult point of ophthalmic treatment, it is undeniable that traditional Chinese medicine has played a great role. Through clinical observation and experimental research, we make full use of the "translation platform" and explore the mechanism of action of traditional Chinese medicine to provide objective basis for clinical medication and application.

In view of the pathogenesis of diabetic retinopathy, the etiology and pathogenesis recognized by Chinese medicine experts is "deficiency in origin and excess in superficiality". "Deficiency in origin" means that most of the DM patients go through yin deficiency and dryness heat in the early stage, deficiency of both qi and yin in the middle period, and deficiency of both yin and yang in the late period; "excess in the superficiality" is manifested as "qi stagnation and blood stasis" persists throughout the microvascular pathological change. Diabetic retinopathy usually occurs at about 10 to 20 years after the occurrence of diabetes mellitus, and "deficiency of both qi and yin, qi stagnation and blood stasis" is the major pathogenesis. According to the pathogenesis of DR, the treatment should focus on activating blood circulation to dissipate blood stasis by solving ocular fundus microaneurysm, minor hemorrhagic foci, hard exudates, edema and other signs to "treat the symptoms"; for those with systemic deficiency of qi and yin, both the symptoms and root cause should be addressed by focusing on supplementing qi and nourishing yin and activating blood circulation to dissipate blood stasis. Based on the above basic principle, lots of studies about DR have been conducted, including comparison of different symptom patterns and experimenting the effects of different therapeutic principles on retinal microangiopathy. However, these studies are not standardized or systematical enough, having different drawbacks.

CONTENTS OF THE INVENTION

One purpose of the present invention is to provide a traditional Chinese medicine composition for the treatment of diabetic retinopathy.

Another purpose of the present invention is to provide the application of the said TCM composition in the preparation of drugs for treating diabetic retinopathy;

Another purpose of the present invention is to provide the application of the said TCM composition in the preparation of drugs for treating macular edema.

The purposes of the present invention are realized by the following technical solutions:

A traditional Chinese medicine (TCM) composition for the treatment of diabetic retinopathy, of which the active pharmaceutical ingredients include *Astragali Radix, Pseudostellariae Radix, Cinnamomi Ramulus, Angelicae Sinensis Radix, Notoginseng Radix* ET *Rhizoma, Dioscoreae Rhizoma, Salviae Miltiorrhizae Radix* ET *Rhizoma, Pheretima, Rehmanniae Radix*, and *Atractylodis Macrocephalae Rhizoma*.

Further, the active pharmaceutical ingredients of the said TCM composition are: *Astragali Radix* 10-80 parts by weight, *Pseudostellariae Radix* 5-30 parts by weight, *Cinnamomi Ramulus* 3-25 parts by weight, *Angelicae Sinensis Radix* 8-60 parts by weight, *Notoginseng Radix* ET *Rhizoma* 2-15 parts by weight, *Dioscoreae Rhizoma* 10-80 parts by weight, *Salviae Miltiorrhizae Radix* ET *Rhizoma* 10-80 parts by weight, *Pheretima* 2-15 parts by weight, *Rehmanniae Radix* 8-60 parts by weight, and *Atractylodis Macrocephalae Rhizoma* 8-60 parts by weight.

More further, the active pharmaceutical ingredients of the said TCM composition are: *Astragali Radix* 15-60 parts by weight, *Pseudostellariae Radix* 6-25 parts by weight, *Cinnamomi Ramulus* 5-20 parts by weight, *Angelicae Sinensis Radix* 10-50 parts by weight, *Notoginseng Radix* ET *Rhizoma* 3-12 parts by weight, *Dioscoreae Rhizoma* 15-60 parts by weight, *Salviae Miltiorrhizae Radix* ET *Rhizoma* 15-60 parts by weight, *Pheretima* 3-12 parts by weight, *Rehmanniae Radix* 10-50 parts by weight, and *Atractylodis Macrocephalae Rhizoma* 10-50 parts by weight.

More further, the active pharmaceutical ingredients of the said TCM composition are: *Astragali Radix* 20-50 parts by weight, *Pseudostellariae Radix* 8-20 parts by weight, *Cinnamomi Ramulus* 8-18 parts by weight, *Angelicae Sinensis Radix* 12-40 parts by weight, *Notoginseng Radix* ET *Rhizoma* 4-10 parts by weight, *Dioscoreae Rhizoma* 20-50 parts by weight, *Salviae Miltiorrhizae Radix* ET *Rhizoma* 20-50 parts by weight, *Pheretima* 4-10 parts by weight, *Rehmanniae Radix* 12-40 parts by weight, and *Atractylodis Macrocephalae Rhizoma* 12-40 parts by weight.

More further, the active pharmaceutical ingredients of the said TCM composition are: *Astragali Radix* 25-40 parts by weight, *Pseudostellariae Radix* 10-18 parts by weight, *Cinnamomi Ramulus* 9-15 parts by weight, *Angelicae Sinensis Radix* 15-30 parts by weight, *Notoginseng Radix* ET *Rhi-* zoma 5-8 parts by weight, *Dioscoreae Rhizoma* 25-40 parts by weight, *Salviae Miltiorrhizae Radix* ET *Rhizoma* 25-40 parts by weight, *Pheretima* 5-8 parts by weight, *Rehmanniae Radix* 15-30 parts by weight, and *Atractylodis Macrocephalae Rhizoma* 15-30 parts by weight.

More further, the active pharmaceutical ingredients of the said TCM composition are: *Astragali Radix* 30 parts by weight, *Pseudostellariae Radix* 12 parts by weight, *Cinnamomi Ramulus* 10 parts by weight, *Angelicae Sinensis Radix* 20 parts by weight, *Notoginseng Radix* ET *Rhizoma* 6 parts by weight, *Dioscoreae Rhizoma* 30 parts by weight, *Salviae Miltiorrhizae Radix* ET *Rhizoma* 30 parts by weight, *Pheretima* 6 parts by weight, *Rehmanniae Radix* 20 parts by weight, and *Atractylodis Macrocephalae Rhizoma* 20 parts by weight;

Or, *Astragali Radix* 28 parts by weight, *Pseudostellariae Radix* 16 parts by weight, *Cinnamomi Ramulus* 9 parts by weight, *Angelicae Sinensis Radix* 28 parts by weight, *Notoginseng Radix* ET *Rhizoma* 5 parts by weight, *Dioscoreae Rhizoma* 35 parts by weight, *Salviae Miltiorrhizae Radix* ET *Rhizoma* 28 parts by weight, *Pheretima* 7 parts by weight, *Rehmanniae Radix* 16 parts by weight, and *Atractylodis Macrocephalae Rhizoma* 28 parts by weight;

Or, *Astragali Radix* 38 parts by weight, *Pseudostellariae Radix* 11 parts by weight, *Cinnamomi Ramulus* 14 parts by weight, *Angelicae Sinensis Radix* 16 parts by weight, *Notoginseng Radix* ET *Rhizoma* 7 parts by weight, *Dioscoreae Rhizoma* 28 parts by weight, *Salviae Miltiorrhizae Radix* ET *Rhizoma* 35 parts by weight, *Pheretima* 5 parts by weight, *Rehmanniae Radix* 28 parts by weight, and *Atractylodis Macrocephalae Rhizoma* 16 parts by weight.

The said *Pseudostellariae Radix* can be replaced with *Ginseng Radix* ET *Rhizoma* or *Panacis Quinquefolii Radix*.

The said *Atractylodis Macrocephalae Rhizoma* should be stir-baked preferentially; and the said *Rehmanniae Radix* should be unprocessed preferentially.

The TCM composition said in the present invention can be the combination of the above APIs that are shattered after mixing. It can also be the extract obtained by mixing and extracting the APIs by the conventional extraction methods, or be the active parts obtained from the extract by further refining and purification process, or be the conventional oral dosage forms prepared by further conventional pharmaceutical process;

Wherein, the said conventional extraction methods include soaking extraction, decoction extraction, refluxing extraction, percolation extraction and ultrasonic extraction, etc.; the extraction solvents include water and 20-95% ethanol solution; the said refining and purification process involves ethanol precipitation, extraction, silica column separation, microporous resin column separation, etc.; the said conventional oral dosage forms include powders, tablets, capsules, granules, oral solutions, pills, etc.

The preparation method of the invented TCM composition is:

Take each active pharmaceutical ingredient proportionally, extract them with water or organic solvent by the conventional extraction methods, and prepare them into conventional oral dosage forms using the conventional pharmaceutical process.

The above conventional extraction methods include any one of the conventional extraction methods such as soaking extraction, decoction extraction, refluxing extraction, ultrasonic extraction and percolation extraction, or the combinations of different extraction methods; the said organic solvent is 20-95% ethanol solution. The said conventional oral dosage forms include granules, tablets, powders, capsules, oral solutions, pills, etc.

To realize the dosage forms said above, it is necessary to add pharmacologically acceptable adjuvants such as fillers, disintegrating agents, lubricants, suspending agents, binding agents, sweeting agents, corrigents, preservatives, ground substances, etc. during their preparation. Fillers include: starch, pregelatinized starch, lactose, mannitol, chitin, microcrystalline cellulose, sucrose, etc.; disintegrating agents include: starch, pregelatinized starch, microcrystalline cellulose, sodium carboxymethyl starch, crospovidone, low-substituted hydroxypropyl cellulose, croscarmellose sodium, etc.; lubricants include: magnesium stearate, sodium dodecyl sulfate, talcum powder, silicon dioxide, etc.; suspending agents include: polyvinylpyrrolidone, microcrystalline cellulose, sucrose, agar, hydroxypropyl methylcellulose, etc.; binding agents include: starch paste, polyvinylpyrrolidone, hydroxypropyl methylcellulose, etc.; sweeting agents include: saccharin sodium, aspartame, sucrose, sodium cyclamate, glycyrrhetinic acid, etc.; corrigents include sweeting agents and various types of essences; preservatives include: nipagin, benzoic acid, sodium benzoate, sorbic acid and sorbates, benzalkonium bromide, chlorhexidine Acetate, *eucalyptus* oil, etc.; ground substances include: PEG6000, PEG4000, insect wax, etc. To realize Chinese medicine pharmacy in the above dosage forms, it is necessary to add other pharmacologically acceptable adjuvants [adjuvants for each dosage from documented in the Chinese Medicine Pharmacy (Fan Biting, Shanghai Scientific & Technical Publishers, December 1997, $1^{st}$ edition)] during their preparation.

For the invented TCM composition, not only the active pharmaceutical ingredients *Astragali Radix, Pseudostellariae Radix, Cinnamomi Ramulus, Angelicae Sinensis Radix, Notoginseng Radix* ET *Rhizoma, Dioscoreae Rhizoma, Salviae Miltiorrhizae Radix* ET *Rhizoma, Pheretima, Rehmanniae Radix* and *Atractylodis Macrocephalae Rhizoma* can be fed in the form of botanical raw material, they can also be fed in the form of extract (effective part). Therefore, the present invention further releases a traditional Chinese medicine composition for the treatment of diabetic retinopathy:

A traditional Chinese medicine composition for the treatment of diabetic retinopathy, which consists of the following active pharmaceutical ingredients: *Astragali Radix* extract 10-80 parts by weight, *Pseudostellariae Radix* extract 5-30 parts by weight, *Cinnamomi Ramulus* extract 3-25 parts by weight, *Angelicae Sinensis Radix* extract 8-60 parts by weight, *Notoginseng Radix* ET *Rhizoma* extract 2-15 parts by weight, *Dioscoreae Rhizoma* extract 10-80 parts by weight, *Salviae Miltiorrhizae Radix* ET *Rhizoma* extract 10-80 parts by weight, *Pheretima* extract 2-15 parts by weight, *Rehmanniae Radix* extract 8-60 parts by weight, and *Atractylodis Macrocephalae Rhizoma* extract 8-60 parts by weight.

More further, the active pharmaceutical ingredients of the said TCM composition are: *Astragali Radix* extract 15-60 parts by weight, *Pseudostellariae Radix* extract 6-25 parts by weight, *Cinnamomi Ramulus* extract 5-20 parts by weight, *Angelicae Sinensis Radix* extract 10-50 parts by weight, *Notoginseng Radix* ET *Rhizoma* extract 3-12 parts by weight, *Dioscoreae Rhizoma* extract 15-60 parts by weight, *Salviae Miltiorrhizae Radix* ET *Rhizoma* extract 15-60 parts by weight, *Pheretima* extract 3-12 parts by weight, *Rehmanniae Radix* extract 10-50 parts by weight, and *Atractylodis Macrocephalae Rhizoma* extract 10-50 parts by weight.

More further, the active pharmaceutical ingredients of the said TCM composition are: *Astragali Radix* extract 25-40 parts by weight, *Pseudostellariae Radix* extract 10-18 parts by weight, *Cinnamomi Ramulus* extract 9-15 parts by weight, *Angelicae Sinensis Radix* extract 15-30 parts by weight, *Notoginseng Radix* ET *Rhizoma* extract 5-8 parts by weight, *Dioscoreae Rhizoma* extract 25-40 parts by weight, *Salviae Miltiorrhizae Radix* ET *Rhizoma* extract 25-40 parts by weight, *Pheretima* extract 5-8 parts by weight, *Rehmanniae Radix* extract 15-30 parts by weight, and *Atractylodis Macrocephalae Rhizoma* extract 15-30 parts by weight.

More further, the active pharmaceutical ingredients of the said TCM composition are: *Astragali Radix* extract 30 parts by weight, *Pseudostellariae Radix* extract 12 parts by weight, *Cinnamomi Ramulus* extract 10 parts by weight, *Angelicae Sinensis Radix* extract 20 parts by weight, *Notoginseng Radix* ET *Rhizoma* extract 6 parts by weight, *Dioscoreae Rhizoma* extract 30 parts by weight, *Salviae Miltiorrhizae Radix* ET *Rhizoma* extract 30 parts by weight, *Pheretima* extract 6 parts by weight, *Rehmanniae Radix* extract 20 parts by weight, and *Atractylodis Macrocephalae Rhizoma* extract 20 parts by weight;

The above API extracts can be the aqueous extracts or organic solvent extracts of each API, or the refined extracts that are obtained from aqueous extracts/organic solvent extracts by further refining and purification process.

The said organic solvent is 20-95% ethanol solution;

The extraction methods used for preparing the above extracts include any one of the conventional extraction methods in this field such as decoction extraction, refluxing extraction, soaking extraction, ultrasonic extraction and percolation extraction, or the combinations of different extract methods; the said refined and purification process involves ethanol precipitation, extraction, silica column separation, microporous resin column separation, etc.

The invented TCM composition mainly consists of *Astragali Radix*, *Pseudostellariae Radix*, *Cinnamomi Ramulus*, *Notoginseng Radix* ET *Rhizoma*, *Salviae Miltiorrhizae Radix* ET *Rhizoma*, *Pheretima* and other drugs. Among them, *Astragali Radix*, *Pseudostellariae Radix* and *Cinnamomi Ramulus* can accelerate blood flow velocity and improve blood quality by warning yang and invigorating spleen as well as nourishing qi and invigorating yang. *Notoginseng Radix* ET *Rhizoma*, *Salviae Miltiorrhizae Radix* ET *Rhizoma* and *Pheretima* arrest bleeding and activate blood circulation as well as dredge collaterals and disperse blood stasis, and thus can reduce platelet aggregation, decrease blood viscosity, scavenge free radicals, alleviate ischemic damage, improve microcirculation and improve the body's tolerance to hypoxia; meanwhile, these drugs can also dilate vessels to increase blood flow volume, improve ischemic status, inhibit blood clotting, promote fibrinolysis, improve blood rheology, reduce plasma viscosity, decrease platelet aggregation, inhibit thrombosis, improve microcirculation and accelerate the blood flow velocity in disturbed microcirculation. Globally, the principle of "nourishing qi and warming yang, activating blood circulation and dredging collaterals" in TCM is satisfied. It has been shown by clinical experiments that, the invented TCM composition has an exact efficacy in patients with macular edema and can effectively improve the patients' visual acuity and visual field and relieve ocular fundus diseases, playing an active role in alleviating macular edema, and superior to Compound Xueshuantong Capsules.

1.2 Diagnostic Criteria: Be developed in accordance with the *International Clinical Classification of DME, EDTRS of Early Treatment Diabetic Retinopathy Study Research Group*, and the "Guidelines for Clinical Studies on the Treatment of Diabetic Retinopathy" in the *Guiding Principles for Clinical Study of New Chinese Medicines*.

Clinical Diagnosis:
(1) Medical history: History of diabetic retinopathy.
(2) Symptoms: In the early stage, there will be mild subjective blurred vision symptom in the early period, and later, there can be visual deterioration of different degrees, with black shadows flying in front of eyes, or distorted vision, and even blindness.
(3) Vital signs: Diabetic macular edema: According to the *International Clinical Classification of DME*, it can be classified as mild, moderate and severe. Mild DME: there are thickening and hard exudate of certain degree at the posterior pole of retina, but far away from the center of the fovea; moderate DME: there are thickening and hard exudate of certain degree at the posterior pole of retina, close to but not involving the center of the fovea; severe DME: there are thickening and hard exudate, involving the center of the fovea.
(4) Fundus fluorescein angiography (FFA): According to the *EDTRS of Early Treatment Diabetic Retinopathy Study Research Group*, DME can be divided into focal, diffuse and cystoid (counted as diffuse subtypes) subtypes: Focal DME: The *macula lutea* shows fluorescence of focal edema, macular telangiectasia and microaneurysm leakage. Diffuse DME: The range is ≥2 PD, involving the foveal avascular zone. There can be massive capillary leakage, diffusing to the superior and inferior hemal arches. Cystoid edema: There is serious focal edema with capillary leakage not diffusing to the superior or inferior hemal arches, but in the late FFA phase, fluorescein leakage is distributed at the periphery of the circinate ring, presenting petaloid or circinate hyperfluorescence.

1.3 Criteria.

(1) Stage I-III diabetic retinopathy with macular edema patients were selected by fundus fluorescein angiography (FFA);

(2) Meeting the WM diagnostic criteria of macular edema;

(3) 18 to 70 years old;

(4) No participation in other clinical trials in the past 2 weeks;

(5) Not taking any therapeutic drug for treating the said disease in the past 2 weeks;

(6) Signing the informed consent form.

1.4 Therapeutic Methods

Patients in the treatment group took the invented TCM composition (prepared by the method in Experiment 1) orally, twice daily and 100 mL per time for three months.

Patients in the control group took Compound Xueshuangtong Capsules orally, 3 capsules per time, 3 times per day. Compound Xueshuangtong Capsules is recorded in the Chinese Pharmacopoeia (2015 version), which consists of *Notoginseng Radix* ET *Rhizoma, Astragali Radix, Salviae Miltiorrhizae Radix* ET *Rhizoma* and *Scrophulariae Radix* and can activate blood circulation to dissipate blood stasis, playing a role in supplementing qi and nourishing yin; it is intended for retinal vein obstruction that is caused by blood stagnation and deficiency of both qi and yin and manifested as visual loss or visual abnormality, ocular fundus congestion, and other diseases.

1.5 Outcome Measures (1) Pre-treatment and post-treatment best corrected visual acuity (international standard visual acuity chart);

(2) OCT-measured thickness of central fovea of macula (TOPCON3DOCT-1000).

(3) Number of microaneurysms counted by fundus photochromy (Topcon TRC-50DX)

(4) Leakage area measured by FFA (Topcon Corp)

Visual acuity efficacy evaluation criteria are developed as follows: According to the international standard visual acuity chart, the best corrected vision is stable within one week. "No light perception" to "light perception" are counted as 2 lines, and the light perception, hand movement, exponent and 0.02, 0.04, 0.06, 0.08, 0.1 intervals are counted as 1 line each. Post-treatment improvement of visual acuity by ≥2 lines are deemed as effective; improvement of visual acuity by 1 line or unchanged visual acuity with certain improvement of fundus condition is deemed as stable; and visual deterioration is deemed as ineffective.

1.6 Statistical Method

Statistical treatment was done using SPSS19.0 software, pre-treatment and post-treatment normally distributed data were compared by the paired-samples t test, non-normally distributed data were compared by non-parametric test, the results were expressed as mean±standard deviation ($\bar{x}\pm s$), and P<0.05 suggested the difference is statistically significant.

2 Results 2.1 Visual Acuity

See Table 1 for the patients' visual acuity distribution before treatment. The changes in the visual acuity at one-month's treatment are shown in Table 2; intra-group comparison was made by t test and compared to pre-treatment, visual acuities in both the treatment group and control group have been improved, and the differences were statistically significant (P<0.05); inter-group comparison was done by $\chi^2$ test, and there was no significant difference in the changes of visual acuity between the treatment group and control group (P>0.05). The changes in the visual acuity at three-month's treatment are shown in Table 3; intra-group comparison was made by t test and compared to pre-treatment, visual acuities in both the treatment group and control group have been improved, and the differences were statistically significant (P<0.05); inter-group comparison was done by $\chi^2$ test, and there was no significant difference in the changes of visual acuity between the treatment group and control group (P>0.05). It shows that, both the treatment group and control group can effectively improve the visual acuity of DME patients, but there was no significance different in the degree of visual acuity improvement between the two groups.

TABLE 1

Pre-treatment Visual Acuity Distribution

| Group | 0.4 and above | 0.25 to 0.4 (incl. 0.25) | 0.15 to 0.25 (incl. 0.15) | 0.15 to 0.1 (incl. 0.1) | 0.06 to 0.1 (incl. 0.06) | 0.02 to 0.06 (incl. 0.02) | 0.02 and below |
|---|---|---|---|---|---|---|---|
| Treatment | 11 | 19 | 15 | 10 | 17 | 6 | 2 |
| Control | 11 | 6 | 7 | 8 | 9 | 3 | 4 |

TABLE 2

Changes in the Visual Acuity after One-month's Treatment

| Group | Number of eyes | Pre-treatment Visual Acuity | Post-treatment Visual Acuity | Number of eyes | Post-treatment Effective | Post-treatment Stable | Post-treatment Ineffective |
|---|---|---|---|---|---|---|---|
| Treatment | 80 | 0.20 ± 0.15 | 0.24 ± 0.22[#] | 80 | 21 (26.25%) | 47 (58.75%) | 12 (15.00%) |
| Control group | 48 | 0.21 ± 0.18 | 0.25 ± 0.25[#] | 48 | 11 (22.92%) | 26 (54.17%) | 11 (22.92%)[*] |

Note:
[#]indicates P < 0.05, as compared to pre-treatment;
[*]indicates P > 0.05, as compared to treatment

TABLE 3

Changes in the Visual Acuity after 3-month's Treatment

| Group | Number of eyes | Pre-treatment Visual Acuity | Post-treatment Visual Acuity | Number of eyes | Post-treatment Effective | Stable | Ineffective |
|---|---|---|---|---|---|---|---|
| Treatment | 80 | 0.20 ± 0.15 | 0.28 ± 0.24# | 80 | 25 (31.25%) | 45 (56.25%) | 10 (12.50%) |
| Control group | 48 | 0.21 ± 0.18 | 0.26 ± 0.23# | 48 | 12 (25.00%) | 26 (54.17%) | 10 (20.83%)* |

Note:
indicates $P < 0.05$, as compared to pre-treatment;
*indicates $P > 0.05$, as compared to treatment 2.2 Thickness of the Central Fovea of Macula All the patients were given OCT examination before and after treatment, and the changes in the thickness of the central fovea of macula are shown in Table 4. Nonparametric test was adopted and the statistical results show that, after one-month's treatment, the descending degree of the central fovea of macula was higher in the treatment group than in the control group, and the difference was statistically significant ($P<0.05$). After three-month's treatment, the descending degree of the central fovea of macula was more significant in the treatment group than in the control group, and the difference was statistically significant ($P<0.05$). It shows that, the regression of macular edema in the treatment group is superior to the control group, and the efficacy is stable.

TABLE 4

Pre- and Post-treatment Thickness of the Central Fovea of Macula ($\bar{x} \pm s$)

| Group | Pre-treatment | After 1-month's treatment | After 3-month's treatment |
|---|---|---|---|
| Treatment | 437.05 ± 96.48 | 317.50 ± 99.96 | 268.20 ± 78.62 |
| Control group | 439.63 ± 100.42 | 355.38 ± 92.06# | 312.25 ± 76.34# |

Note:
indicates $P < 0.05$, as compared to treatment 2.3 Number of Microaneurysms The number of retinal microaneurysms was observed by fundus photochromy before and after treatment, as shown in Table 5. Non-parametric test was conducted, which showed that, after one-month's treatment, there was significant difference in the changes of the number of microaneurysms between the treatment group and control group ($P>0.05$), and after three-month's treatment, the treatment group showed a decreasing tendency of microaneurysms significantly superior to that of the control group, and the difference was statistically significant ($P<0.05$). It suggests that, this invented TCM composition combined with laser in the treatment of DR shows itself advantages in the changes of microaneurysms at 3 months after treatment.

TABLE 5

Pre- and Post-treatment Numbers of Microaneurysms ($\bar{x} \pm s$)

| Group | Pre-treatment | After 1-month's treatment | After 3-month's treatment |
|---|---|---|---|
| Treatment | 22.83 ± 12.84 | 20.86 ± 10.33 | 18.75 ± 9.96 |
| Control group | 23.17 ± 12.89 | 21.96 ± 11.46* | 21.58 ± 10.96# |

Note:
*indicates $P > 0.05$, as compared to treatment;
indicates $P < 0.05$, as compared to treatment 2.4 Leakage Area The changes in the retinal leakage area were measured by FFA before and after treatment, as shown in Table 6. Non-parametric test was conducted, which showed that, after one-month's treatment, the degree of leakage area reduction in the treatment group was significantly superior to that of the control group, and the difference was statistically significant ($P<0.05$); after three-month's treatment, the degree of leakage area reduction was more significant in the treatment group than in the control group, and the difference was statistically significant ($P<0.05$). It shows that, the treatment group can reduce the leakage area more effectively, and the efficacy is stable.

TABLE 6

Pre- and Post-treatment Leakage Areas ($\bar{x} \pm s$)

| Group | Pre-treatment | After 1-month's treatment | After 3-month's treatment |
|---|---|---|---|
| Treatment | 1.71 ± 0.83 | 1.33 ± 0.82 | 1.28 ± 0.83 |
| Control group | 1.72 ± 0.92 | 1.50 ± 0.80# | 1.49 ± 0.79# |

Note:
indicates $P < 0.05$, as compared to treatment

3 Conclusion

The invented TCM composition has an exact efficacy in patients with macular edema and can effectively improve the patients' visual acuity, decrease the thickness of the central fovea of macula, reduce leakage area and decrease the number of microaneurysms.

EXPERIMENT 2 EXPERIMENTAL STUDY OF THE INVENTED TCM COMPOSITION IN THE TREATING RETINOPATHY OF DIABETIC RATS (I)

1 Experimental Methods 1.1 Modeling and Grouping: VAF-grade male SD rats, 140 to 160 g in weight, purchased from Vital River Laboratory Animal Technology Co., Ltd. were selected and fed in the laboratory animal center of the Clinical Medicine Institute, China-Japan Friendship Hospital. In the experiment period, food and water were provided ad libitum. Standard rat food was purchased from Beijing Jiujiang Pellet Feed Factory, and the rat cages and paddings were purchased from Beijing Kelin Laboratory Animal Services Center. After one-week's adaptive feeding, a total 70 rats were 180 to 200 g in weight. Except for animals in the normal group, rats in other groups were fasted for 12 hours before modelling and injected with streptozotocin (STZ) via intraperitoneal injection. 1% STZ solution was prepared with sterile 0.01 mmol/L sodium citrate buffer solution at pH 4.4 right before use and injected via the left lower abdominal cavity according to the rat weight of 65 mg/kg. Rats in the normal group was injected with normal saline of the same volume. 72 hours later, blood was collected via caudal vein to measure blood glucose using a rapid glucose meter (Roche blood glucose meter, Roche ACCU-CHEK Active test strips). Rats with non-fasting blood glucose ≥16.7 mmol/L were used as the diabetic rat model.

After successful modelling, diabetic rats were randomized into the model group (10 rats), experiment group (10 rats, given the TCM composition prepared according to Experiment 1) and normal group (10 rats). The experiment lasted 300 days.

1.2 Observation Methods and Outcome Measures: After execution, the eyeballs of rats were fixed in 4% paraformaldehyde solution to prepare retinal digest preparation specimens, which were then stained with PAS-H for vascular endothelial cell (E) counting, pericyte (P) counting and E/P comparison. Paraffin-embedded retinal sections were prepared to observe the expression of vascular endothelial growth factor (VEGF), intercellular adhesion molecule-1 (ICAM-1), pigment epithelium-derived factor (PEDF) and advanced glycation end products (AGEs). Fresh eyeball paste was performed with RT-PCR to test VEGFmRNA, PEDFmRNA and ICAM-1mRNA levels, as well as the mRNA level of RAGE. The image analyzer was used to measure immunohistochemical color intensity for quantitative analysis. And the data was analyzed and processed using SPSS 13.0 statistical software.

2 Experimental Results 2.1 Endothelial Cell (E) Counting, Pericyte (P) Counting and E/P Comparison of Retinal Digest See Table 7 for the results.

TABLE 7

Endothelial Cell (E) Counting Pericyte (P) Counting and E/P Comparison of Retinal Digest

| Group | n | Endothelial Cell (E) | Pericyte (P) | E/P |
|---|---|---|---|---|
| Normal group | 10 | 796.40 ± 18.48 | 203.50 ± 18.54 | 3.95 ± 0.45 |
| Model group | 10 | 919.00 ± 10.22* | 81.10 ± 10.06* | 11.50 ± 1.56* |
| Experiment group | 9 | 874.78 ± 15.75*△ | 125.22 ± 15.75*△ | 7.10 ± 0.98*△ |

Note:
Model group and experiment group vs. normal group: *$P < 0.01$;
treatment group vs. model group: △$P < 0.01$.

According to the above results, the proliferation of endothelial cells was more significant in the model group than in the normal group, but pericytes were significantly reduced (P<0.01). However, compared to the model group, such changes in the experiment group and normal group were significantly alleviated (P<0.01), and there were significant differences in E/P. It suggests that, the investigational medicine plays a role in inhibiting endothelial cell proliferation and reducing selective loss of pericytes, subsequently delaying the progression of diabetic retinopathy.

2.2 Study on Mechanism of Action

As shown by the study, the invented TCM composition can reduce the deposition of AGEs in endothelial cells, pericytes and basement membrane and reduce the stimulation to endothelial cells by reducing the expression of AGEs and RAGE mRNA in the retina of diabetic rats, and subsequently reduce the occurrence of VEGF to relieve vascular wall functional disorder. By reducing the expression retinal capillary ICAM-1 and retinal ICAM-1 mRNA, it can reduce adhesion of leukocytes to vascular endothelial cells. By reducing the expression of retinal and capillary VEGF and retinal VEGF mRNA and decreasing vascular permeability, it can up-regulate ICAM-1 expression. In addition, it can increase expression of retinal PEDF and retinal PEDF mRNA to inhibit neovascularization.

EXPERIMENT 3 EXPERIMENTAL STUDY OF THE INVENTED TCM COMPOSITION IN THE TREATING RETINOPATHY OF DIABETIC RATS (II)

1 Materials and Methods 1.1 Laboratory Animals and Grouping

48 SPF-grade SD rats, male, 6 weeks old, (220±20) g in weight, were purchased from Huafukang Biotechnology Co., Ltd. After one-week's adaptive feeding, the rats were randomized into the modeling group (36 rats) and normal group (12 rats). The rats were fasted for 12 hours before modeling and given 1% STZ solution according to the body weight of 60 mg/kg via one intraperitoneal injection to induce experiment diabetic rat models. Rats in the normal group were injected with normal saline of the same volume. Blood glucose was monitored 72 hours later, blood was collected via caudal vein, and the modeling was deemed as successful when the blood glucose was ≥16.7 mmol/L for 3 consecutive days; after successful modeling, rats were randomized into the model group (12 rats), TCM composition experiment group (abbreviated as the experiment group, containing 12 rats) and Doxium group (abbreviated as the control group, containing 12 rats). Rats in the experiment group and control group were dosed on the next day after successful modeling. The administered dose of the experiment group was 10 ml/(kg·d) and that of the control group was 250 mg/(kg·d), with the Doxium powders dissolved in 2 mL distilled water. Rats in the normal group and model group were given 2 mL of distilled water in the intragastric manner. In the experiment period, all the rats were given food and drinking water at regular times each day; the changes in the body weight and blood glucose of rats were monitored monthly. And sampling was performed 9 months later.

1.2 Retinal Vascular Digest Preparation

An eyeball was randomly selected from 6 rats of each group to prepare into retinal vascular digest preparation specimens by the following preparation method: Fix the eyeball in 4% paraformaldehyde solution for 48 hours, then gently rinse it with running water for 5 min, cut the sclera open circularly via the ora serrata and remove the anterior segment of eye; cut the posterior optic cup into 3 pieces in the orange petal shape using the optic papilla as the center, and gently isolate the retina; rinse the retina with BPS (0.01 mol/L, pH7.4) for 10 min; Digest the retina with 3% trypsin in a 37° C. incubator for 3 hours; transfer the digested retina to distilled water and rinse and oscillate it for multiple times to leave only a layer of transparent retinal vascular net; rinse the net and title it onto the slide. PAS staining was conducted and the slide was observed under the Olympus light microscope.

1.3 Preparation of Retinal Paraffin Section Specimen for Light Microscopy

Bilateral eyeballs of the rest 6 rats in each group were taken to prepare paraffin sections: Place the eyeball and optic nerves into 4% paraformaldehyde solution (4° C., 48 h) for fixation, and then cut the wall of eyeball open along the corneal limbus, remove the cornea, crystalline lens and vitreous body, dehydrate the tissues in gradient alcohol, make them transparent with xylene, embed them in paraffin, and cut into serial sections 10 pin thick, carry out HE staining and immunohistochemical staining, and observe the sections under the Olympus light microscope.

1.4 Retinal Electron Microscopic Observation

Another eyeball of the first 6 rats of each group were taken and fixed in 2.5% glutaraldehyde (4° C.) for 72 hours, after which a tissue 2 mm×2 mm was dissected from the retinal central area. The tissue was then fixed in 1% osmic acid, dehydrated with acetone grade by grade, embedded in Epon812 epoxy resin, and cut into 1 pin semithin sections for light microscope positioning. Then ultrathin sections were made, given double staining with uranyl acetate and observed under Hitachi H-600 transmission electron microscope.

1.5 Statistical Analysis

All the data collected in the experiment were analyzed and processed by SPSS19.0 statistical software using t test, analysis of variance or non-parametric test, the statistical results were expressed as mean±standard deviation, and $\alpha=0.05$ was used as the test criterion, i.e., the difference is deemed as statistically significant when $P \leq 0.05$.

2 Results 2.1 Body Weight and Blood Glucose

See Table 8 for the results. As observed in the experiment period, compared to rats in the normal group, those in the model group grew slowly with withered hair, emaciated shape, increased urine volume and thin sloppy stool. There was no significant difference in the blood glucose before modeling between groups (P>0.05); compared to the normal group, post-modeling rats had significantly increased blood glucose at different time periods, showing significant difference (P<0.01).

TABLE 8

Changes in the Blood Glucose of Rats of Each Group at Different Time Periods (unit. mmol/L) ($\bar{x} \pm s$)

| Time | Normal group | Experiment group |
|---|---|---|
| Pre-modeling | 6.05 ± 0.49 | 6.09 ± 0.45$^\Delta$ |
| Post-modeling | 6.42 ± 0.15 | 28.03 ± 2.29* |
| 1 month | 6.92 ± 0.94 | 29.30 ± 1.85* |
| 2 months | 6.63 ± 0.71 | 30.29 ± 2.43* |
| 3 months | 6.48 ± 0.58 | 31.16 ± 1.62* |
| 4 months | 6.18 ± 0.49 | 29.04 ± 1.95* |
| 5 months | 5.53 ± 0.56 | 29.00 ± 2.74* |
| 6 months | 5.12 ± 0.67 | 29.71 ± 3.13* |
| 7 months | 5.58 ± 0.43 | 29.99 ± 1.57* |
| 8 months | 6.00 ± 0.25 | 30.01 ± 2.95* |
| 9 months | 5.95 ± 0.46 | 29.63 ± 3.19* |

Figure 1:
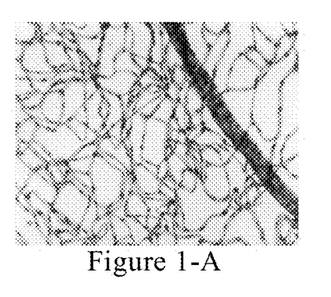
FIG. 1 Microscopic Observation Results of Retinal Vascular Digest Preparation
  A. Normal group; B. Model group; C. Experiment group; D. Control group FIG. 2 Light Microscopic Observation Results of Retinal Paraffin Section
  A. Normal group; B. Model group; C. Experiment group; D. Control group FIG. 3 Immunohistochemical Staining Result of Retinal Paraffin Section
  A. Normal group; B. Model group; C. Experiment group; D. Control group FIG. 4 Electron Microscopic Observation Result of Retina
  A. Normal group; B. Model group; C. Experiment group; D. Control group EXPERIMENT 1 CLINICAL EXPERIMENT OF THE INVENTED TCM COMPOSITION IN THE TREATMENT OF DIABETIC RETINOPATHY 1 Materials and Methods 1.1 General Information. The subjects of the study were 80 patients who were confirmed as diabetic macular edema (DME) in the period from January 2014 to July 2015, including 49 in the treatment group (80 eyes) and 31 in the control group (48 eyes). In the treatment group, there were 18 males (29 eyes) and 31 females (51 eyes), at a median age of 59.80±10.21 years and with a course of disease of 7.41±4.62 years; in the control group, there were 11 males (17 eyes) and 20 females (31 eyes), at a median age of 57.63±12.12 years and with a course of disease of 8.17±5.34 years.

Note:
$^\Delta$indicates P > 0.05, as compared to the normal group,
*indicates P < 0.05, as compared to the normal group 2.2 Retinal Vascular Digest Preparation Retinal vascular digest preparation was observed under the microscope: For normal rats, the retinal capillaries were distributed regularly, ran straight, and were uniform in the diameter and thickness; endothelial cells were usually located at the central part of capillary, with a big, lightly-stained nucleus that was oval or irregular in shape and had the long axis in parallel with the capillary; pericytes were located outside the lumen of capillary, with a relatively small, deeply-stained nucleus that was globular or triangular in shape (see FIG. 1-A). For rats in the model group, the retinal vascular nets were disorderly arranged and ran in an extremely irregular manner, not uniform in the diameter or thickness, with multiple capillaries twisted into loops and segmentally inflated; the nuclei of pericytes became pyknotic, endothelial cells and extracellular matrix were significantly proliferative, and characteristic changes of diabetic retinopathy such as cell-free capillaries, shadow pericytes and endothelial cell apoptosis can be noted (see FIG. 1-B). After invention in the experiment group (see FIG. 1-C) and control group (see FIG. 1-D), retinal microvascular changes were significantly prevented or delayed: there was no cell-free capillary, shadow pericyte or other typical changes of early DR, capillaries were distributed regularly and relatively uniform in the thickness, without any twisting or dilatation.

2.3 HE Staining of Retinal Paraffin Sections

Figure 2:
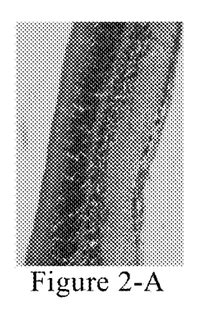

The HE staining of retinal paraffin sections were observed under the light microscope: For rats in the normal group, tissues at different layers of retina were stratified a clearly and arranged orderly (see FIG. 2-A). For rats in the model group, tissues at different layers of retina were distributed in an extremely disordered manner, capillaries were significantly dilated, edema at the nerve fiber layer was thickened, retinal ganglion cells were decreased, vacuolar degeneration, karyopyknosis and chromatin marginalization were noted, some retinal ganglion cells became necrotic, and there were karyolysis, edema at the inner plexiform layer and vacuolar degeneration at the inner nuclear layer (see FIG. 2-B). For rats in the experiment group, the retinal stroma was mildly edematous, but the cells were basically arranged in order (see FIG. 2-C). For rats in the control group, the retinal net structure was loose, internal and external granular layers were arranged in a disordered manner, capillaries were dilated, and interstitial edema can be noted (see FIG. 2-D).

2.4 Immunohistochemistry of Retinal Paraffin Sections

Figure 3:
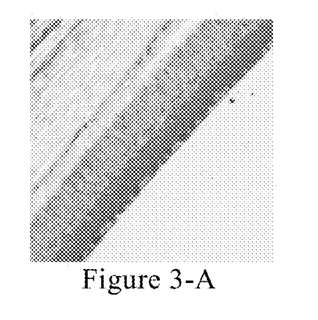

Vascular endothelial growth factors (VEFG) labeled and stained by the immunohistochemical method were extensively expressed in the retina of rats, with the positive expression site being brownish yellow or tan in color. Comparison of gray-scale values of VEGF expression in the retinas of each group: The expression was significantly higher in the model group (see FIG. 3-A) than in the normal group (see FIG. 3-B) (P<0.01); the VEGF expressions in the experiment group (see FIG. 3-C) and control group (see FIG. 3-D) were significantly lower than that in the model group (P<0.01), showing statistically significant differences; however, the difference between the experiment group and control group was not significant (see Table 9).

TABLE 9

Inter-group Comparison of Whole-layer Retinal VEGF Expression (Gray-scale values) ($\bar{x} \pm s$)

| Group | Number of eyes | Mean Optical Density Value |
|---|---|---|
| Normal group | 6 | 0.28 ± 0.12 |
| Model group | 6 | 0.77 ± 0.10* |
| Experiment group | 6 | 0.42 ± 0.86*#$^\Delta$ |
| Control group | 6 | 0.43 ± 0.09*# |

Note:
*indicates P < 0.01, as compared to the normal group;
indicates P < 0.01, as compared to the model group;
$^\Delta$indicates P > 0.05 for experiment group vs. control group.

2.5 Retinal Electron Microscopy

Figure 4:
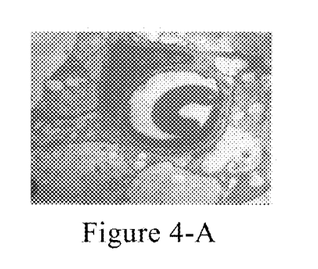

Retinal ultrastructure observation: The retinal endothelial cells of normal rats were shaped normally, spindle-shaped, with complete intracellular junctions and continued but not thick basement membrane. Microtubules and mitochondria at the nerve fiber layer were clear, ganglion cells were oval a big and obvious nucleus, lots of rough endoplasmic reticula, polyribosomes and mitochondria in the cytoplasm and plenty of projections on the cell surface (see FIG. 4-A). For rats in the model group, the retinal capillary endothelial cells were significantly swelling, the cell bodies were rounding and protruding towards the lumina, there were mitochondrial swelling, vacuolization, basement membrane thickening, ganglion cell body deformation, significant karyopyknosis and nuclear envelope breakdown, lots of vacuoles of varying sizes can be seen in the cytoplasm, mitochondria were swelling, projections on the cell surface were significantly reduced, and polyribosomes and rough endoplasmic reticula were significantly reduced (see FIG. 4-B). For animals in the experiment group, the vascular walls of retinal capillaries were still regular and smooth, basement membranes were slightly thickened, a few pericytes were edematous, some endothelial cells were mildly proliferative, ganglion cell bodies were deformed, mitochondria were mildly swelling, and the structures were slightly ill-defined (see FIG. 4-C). For rats in the control group, the vascular walls of retinal capillaries were still regular and smooth, basement membranes were thickened, a few pericytes were edematous, some endothelial cells were swelling, some mitochondria can be noted with vacuolization, ganglion cell bodies were deformed, mitochondria were mildly swelling with chromatinolysis, and the intercrislal space were more seriously dilated and even disappeared (see FIG. 4-D).

3 Conclusion

There was significant pathological damage in the retinal vessels of experimental diabetic rats; the invented TCM composition has a certain protective effect on the retinal vessels of diabetic rats and can inhibit VEGF expression in the retinas of diabetic rats to help reduce damage on retinal vessels.

EXPERIMENT 4 EXPERIMENTAL STUDY OF THE INVENTED TCM COMPOSITION FOR TREATING OPTIC NERVE CONDUCTION IN DIABETIC RATS

1 Experimental Methods 1.1 Modeling and Grouping

The modeling method was the same as that in Experiment 2.

After successful modeling, diabetic rats were randomized into the model group (5 rats), experiment group (5 rats, given TCM composition prepared according to Experiment 1), and normal group (5 rats). The experiment lasted 300 days.

1.2 Observation Methods and Outcome Measures: After the animals were executed, retinal tissue sections were prepared for morphological examination; the ultrastructure of retinal nerve cells were observed under the electron microscope; the expression level of retinal glial fibrillary acidic protein (GFAP) mRNA was tested by the RT-PCR method; the apoptosis of retinal ganglion cells (RGCs) and inner nuclear layer cells were tested by the TUNEL method, with the number of apoptotic cells counted; the expressions of GFAP, glutamate-aspartate transporter (GLAST), glutamine synthetase (GS) and neurotrophic factor-3 (NT-3) in the retina were tested by the immunochemical technique, LASB to observe the changes in the function of RGCs and inner nuclear layer cells. The methods for data analysis were the same as those in the Experiment 2.

2 Experimental Results 2.1 Study on the Apoptosis of RGCs:

Determination of apoptosis-positive RGCs: Cells with the nucleus stained brownish yellow (tan) were deemed as apoptosis-positive. Counting of apoptosis-positive RGCs: Under the high-power (10×40 times) binocular microscope, 5 consecutive visual fields were taken along one side of the optic disk towards the ora serrata, of which the mean was counted as apoptotic RGCs/HP. 3 consecutive sections were read, of which the mean RGCs count was adopted as the RGCs cell apoptosis count of the tested sample. The results of this experiment showed that: as tested by the TUNEL method, rat retinal apoptosis-positive cells were only noted at the RGCs layer and inner nuclear layer. See Table 10 for the effects on RGCs apoptosis in each group.

TABLE 10

Effects of the Invented Composition on RGCs Apoptosis ($\bar{x} \pm s$)

| Group | Case No. | RGCs Apoptosis Count |
|---|---|---|
| Normal group | 5 | 4.92 ± 0.16 |
| Model group | 5 | 11.98 ± 1.56* |
| Experiment group | 5 | 8.14 ± 0.88*# |

Note:
*indicates $P < 0.01$, as compared to the normal group;
indicates $P < 0.05$, as compared to the model group The above results showed that, compared to normal rats, the RGCs apoptosis count of rats in the model group was significantly increased ($P<0.01$); compared to the model group, the RGCs apoptosis count of the experiment group was significantly decreased ($P<0.05$), suggesting that the invented composition can inhibit RGCs apoptosis of modeling rats and have a neuroprotective effect on them.

2.2 Study on Mechanism of Action

As shown by the study, the invented TCM composition inhibits GFAP overexpression in Müller cells, suppresses reactive proliferation of glial cells, decreases the effects of DM on the function of Müller cells, and reduces the damage on retinal neurons; it can promote GLAST and GS expressions in Müller cells, scavenge excessive extracellular glutamate timely and effectively, and reduce excitotoxicity caused by high-concentration glutamate; in addition, it can promote the expression of neurotrophic factor NT-3 to reduce nerve cell apoptosis.

EXPERIMENT 5 EXPERIMENTAL STUDY OF THE INVENTED TCM COMPOSITION FOR TREATING IRIDIC MICROCIRCULATION DISEASE IN DIABETIC RATS

1 Experimental Methods 1.1 Modeling and Grouping:

The modeling was the same as that of Experiment 2.

After successful modeling, diabetic rats were randomized into the model group (20 rats), experiment group (30 rats, given the TCM composition prepared according to Experiment 1), control group (Doxium group, 20 rats) and normal group (12 rats). The experiment lasted 300 days.

1.2 Observation Methods and Outcome Measures: The iris blood flow velocity, diameter of iris vessels, density of iris microvessels, endothelial structure of iris microvessels, permeability of iris microvessels and iris unit area blood perfusion volume were observed by the iris vascular perfusion scan and iris fluorescein angiography.

2 Experiment Results

2.1 Iris Blood Flow Velocity: See Table 11 for the results.

As shown by the results, the iris blood flow velocity was stable in the normal group, but significantly decreased in the model group; compared to the model group, the iris blood flow velocity in the experiment group was significantly increased ($P<0.01$); however, there was no statistically significant difference between the Doxium group and model group.

TABLE 11

Comparison of Pre- and Post-treatment Iris Blood Flow Velocities ($\bar{x} \pm s$)

| | Blood Flow Velocity Index (min) | |
|---|---|---|
| Group | Pre-treatment | Post-treatment |
| Normal group | 1.00 ± 0 | 1.20 ± 0.24 |
| Model group | 1.12 ± 0.25 | 3.52 ± 0.33** |
| Experiment group | 1.02 ± 0.05 | 2.47 ± 0.67$^{\triangle\triangle**}$ |
| Control group | 1.07 ± 0.07 | 3.25 ± 0.81** |

Note:
**indicates $P < 0.01$, as compared to the normal group;
$^{\triangle\triangle}$indicates $P < 0.01$, as compared to the model group.

2.2 Diameter of Iris Vessels: See Table 12 for the results.

The results showed that, the iris vessels in the normal group were uniform in the diameter; compared to the normal group, iris vessels in the model group were significantly dilated; compared to the model group, iris vessels in the experiment group were significantly reduced in the diameter ($P<0.01$); there was no statistically significant difference between the Doxium group and model group.

TABLE 12

Comparison of Pre- and Post-treatment Diameters of Iris Vessels ($\bar{x} \pm s$)

| | Diameter of Vessel (μm) | |
|---|---|---|
| Group | Pre-treatment | Post-treatment |
| Normal group | 14.82 ± 4.09 | 15.34 ± 2.53 |
| Model group | 15.49 ± 3.05 | 52.53 ± 14.34** |
| Experiment group | 15.14 ± 5.19 | 34.80 ± 10.87$^{\triangle\triangle**}$ |
| Normal group | 14.82 ± 4.09 | 15.34 ± 2.53 |

Note:
**indicates $P < 0.01$, as compared to the normal group;
$^{\triangle\triangle}$indicates $P < 0.01$, as compared to the model group.

2.3 Iris Blood Perfusion Volume: See Table 13 for the results.

According to the results, laser Doppler scanning imaging showed sufficient iris unit area blood perfusion volume in the normal group and the scanning imaging was uniform; compared to the normal group, the iris blood perfusion volume in the model group was significantly decreased ($P<0.01$); compared to the model group, the iris blood perfusion volume in the treatment group was increased ($P<0.05$); and there was no statistically significant difference between the control group and model group.

TABLE 13

Pre- and Post-treatment Unit Area Blood Perfusion Volumes ($\bar{x} \pm s$)

| | Iris Unit Area Blood Perfusion Volume | |
|---|---|---|
| Group | Pre-treatment | Post-treatment |
| Normal group | 646.70 ± 162.31 | 628.19 ± 64.53 |
| Model group | 599.26 ± 91.77 | 107.37 ± 15.62** |
| Experiment group | 609.68 ± 57.66 | 200.02 ± 90.71$^{\triangle**}$ |
| Control group | 607.45 ± 194.19 | 133.71 ± 6.89** |

Note:
**indicates $P < 0.01$, as compared to the normal group;
$^{\triangle}$indicates $P < 0.05$, as compared to the model group.

As shown by the above results, the invented investigational composition can accelerate iris blood flow, inhibit abnormal vascular dilation and improve abnormally increased permeability status of iris microvessels; in addition, it can increase unit area blood perfusion to relieve ischemic status.

SPECIFIC EMBODIMENTS OF THE INVENTION

Embodiment 1

Active pharmaceutical ingredients (APIs): *Astragali Radix* 30 g, *Pseudostellariae Radix* 12 g, *Cinnamomi Ramulus* 10 g, *Angelicae Sinensis Radix* 20 g, *Notoginseng Radix ET Rhizoma* 6 g, *Dioscoreae Rhizoma* 30 g, *Salviae Miltiorrhizae Radix ET Rhizoma* 30 g, *Pheretima* 6 g, *Rehmanniae Radix* 20 g and stir-baked *Atractylodis Macrocephalae Rhizoma* 20 g;

Preparation method: Take the APIs proportionally, add water and decoct twice (1.5 hours each time), mix and filtrate the decoctions, and concentrate the mixed decoction into 200 mL;

Dosage and administration: Twice daily (once in the morning, once in the evening), 100 mL each time.

Embodiment 2

Active pharmaceutical ingredients (APIs): *Astragali Radix* 28 g, *Pseudostellariae Radix* 16 g, *Cinnamomi Ramulus* 9 g, *Angelicae Sinensis Radix* 28 g, *Notoginseng Radix ET Rhizoma* 5 g, *Dioscoreae Rhizoma* 35 g, *Salviae Miltiorrhizae Radix ET Rhizoma* 28 g, *Pheretima* 7 g, *Rehmanniae Radix* 16 g and stir-baked *Atractylodis Macrocephalae Rhizoma* 28 g;

Preparation method: Take the APIs proportionally, perform ultrasonic extraction with 70% ethanol twice (1 hour in the first time and 0.5 hour in the second time), mix and filtrate the extracts, concentrate the mixed extract by decompressing, mix the concentrated extract with dextrin (as the excipient) according to the ratio of 3:1, blend well, prepare the mixture into granules, dry them and get the granule preparation.

Embodiment 3

Active pharmaceutical ingredients (APIs): *Astragali Radix* 38 g, *Pseudostellariae Radix* 11 g, *Cinnamomi Ramulus* 14 g, *Angelicae Sinensis Radix* 16 g, *Notoginseng Radix ET Rhizoma* 7 g, *Dioscoreae Rhizoma* 28 g, *Salviae Miltiorrhizae Radix ET Rhizoma* 35 g, *Pheretima* 5 g, *Rehmanniae Radix* 28 g and stir-baked *Atractylodis Macrocephalae Rhizoma* 16 g;

Preparation method: Take the APIs proportionally, add water and decoct twice (1.5 hours each time), mix and filtrate the decoctions, and prepare the mixed decoction into oral solution according to the conventional pharmaceutical process.

Embodiment 4

Active pharmaceutical ingredients (APIs): *Astragali Radix* 22 g, *Panax ginseng* 18 g, *Cinnamomi Ramulus* 9 g, *Angelicae Sinensis Radix* 35 g, *Notoginseng Radix* ET *Rhizoma* 5 g, *Dioscoreae Rhizoma* 45 g, *Salviae Miltiorrhizae Radix* ET *Rhizoma* 22 g, *Pheretima* 8 g, *Rehmanniae Radix* 15 g and *Atractylodis Macrocephalae Rhizoma* 35 g;

Preparation method: Take the APIs proportionally, add water and perform refluxing extraction twice (1.5 hours each time), mix, filtrate and concentrate the decoctions, add 60% ethanol solution and perform ethanol precipitation, let the precipitated decoction stand still, filtrate and concentrate the decoction, dry it by decompressing, and mix it with dextrin (as the excipient) according to the ratio of 3:1, blend well, prepare the mixture into granules, dry them and get the granule preparation.

Embodiment 5

Active pharmaceutical ingredients (APIs): *Astragali Radix* 45 g, *Panax ginseng* 10 g, *Cinnamomi Ramulus* 15 g, *Angelicae Sinensis Radix* 13 g, *Notoginseng Radix* ET *Rhizoma* 8 g, *Dioscoreae Rhizoma* 22 g, *Salviae Miltiorrhizae Radix* ET *Rhizoma* 48 g, *Pheretima* 5 g, *Rehmanniae Radix* 38 g and *Atractylodis Macrocephalae Rhizoma* 15 g;

Preparation method: Take the APIs proportionally, mix well, shatter into pieces, pass them through 60- to 80-mesh screen, and prepare into powders.

Embodiment 6

Active pharmaceutical ingredients (APIs): *Astragali Radix* 16 g, American *ginseng* 24 g, *Cinnamomi Ramulus* 6 g, *Angelicae Sinensis Radix* 45 g, *Notoginseng Radix* ET *Rhizoma* 4 g, *Dioscoreae Rhizoma* 55 g, *Salviae Miltiorrhizae Radix* ET *Rhizoma* 16 g, *Pheretima* 10 g, *Rehmanniae Radix* 12 g and *Atractylodis Macrocephalae Rhizoma* 45 g;

Preparation method: Take the APIs proportionally, add water and decoct twice (1.5 hours each time), mix and filtrate the decoctions, and prepare the mixed decoction into oral solution according to the conventional pharmaceutical process.

Embodiment 7

Active pharmaceutical ingredients (APIs): *Astragali Radix* 55 g, *Pseudostellariae Radix* 7 g, *Cinnamomi Ramulus* 18 g, *Angelicae Sinensis Radix* 12 g, *Notoginseng Radix* ET *Rhizoma* 11 g, *Dioscoreae Rhizoma* 18 g, *Salviae Miltiorrhizae Radix* ET *Rhizoma* 55 g, *Pheretima* 4 g, *Rehmanniae Radix* 45 g and stir-baked *Atractylodis Macrocephalae Rhizoma* 12 g;

Preparation method: Take the APIs proportionally, perform ultrasonic extraction with 70% ethanol twice (1 hour in the first time and 0.5 hour in the second time), mix and filtrate the extracts, concentrate the mixed extract by decompressing, purify the concentrated solution in D101 macroporous resin column, elute the purified solution with 2BV water first, then elute it with 5BV 50% ethanol solution, collect 50% ethanol eluent, recover ethanol, add conventional adjuvants into the extract according to the conventional pharmaceutical process, and prepare them into tablets.

Embodiment 8

Active pharmaceutical ingredients (APIs): *Astragali Radix* 12 g, *Pseudostellariae Radix* 28 g, *Cinnamomi Ramulus* 4 g, *Angelicae Sinensis Radix* 55 g, *Notoginseng Radix* ET *Rhizoma* 3 g, *Dioscoreae Rhizoma* 75 g, *Salviae Miltiorrhizae Radix* ET *Rhizoma* 12 g, *Pheretima* 14 g, *Rehmanniae Radix* 9 g and stir-baked *Atractylodis Macrocephalae Rhizoma* 55 g;

Preparation method: Take the APIs proportionally, add water and decoct twice (1.5 hours each time), mix and filtrate the decoctions, concentrate the filtrated solution, dry the concentrated solution by decompressing, mix it with dextrin (as the excipient) according to the ratio of 3:1, blend well, prepare the mixture into granules, dry them and get the granule preparation.

Embodiment 9

Active pharmaceutical ingredients (APIs): *Astragali Radix* 75 g, *Pseudostellariae Radix* 6 g, *Cinnamomi Ramulus* 24 g, *Angelicae Sinensis Radix* 8 g, *Notoginseng Radix* ET *Rhizoma* 14 g, *Dioscoreae Rhizoma* 12 g, *Salviae Miltiorrhizae Radix* ET *Rhizoma* 75 g, *Pheretima* 3 g, *Rehmanniae Radix* 55 g and stir-baked *Atractylodis Macrocephalae Rhizoma* 10 g;

Preparation method: Take the APIs proportionally, add 75% ethanol 6 times in volume and perform refluxing extraction twice (1.5 hours each time), mix and filtrate the extracts, add in conventional adjuvants, and prepare the mixture into oral solution.

Embodiment 10

Active pharmaceutical ingredients (APIs): *Astragali Radix* extract 30 g, *Pseudostellariae Radix* extract 12 g, *Cinnamomi Ramulus* extract 10 g, *Angelicae Sinensis Radix* extract 20 g, *Notoginseng Radix* ET *Rhizoma* extract 6 g, *Dioscoreae Rhizoma* extract 30 g, *Salviae Miltiorrhizae Radix* ET *Rhizoma* extract 30 g, *Pheretima* extract 6 g, *Rehmanniae Radix* extract 20 g and *Atractylodis Macrocephalae Rhizoma* extract 20 g;

The above API extracts are aqueous extracts obtained by decocting the APIs with water. The aqueous API extracts are mixed together, filtrated and prepared into oral solution according to the conventional pharmaceutical process.

Embodiment 11

Active pharmaceutical ingredients (APIs): *Astragali Radix* extract 28 g, *Panax ginseng* extract 16 g, *Cinnamomi Ramulus* extract 9 g, *Angelicae Sinensis Radix* extract 28 g, *Notoginseng Radix* ET *Rhizoma* extract 5 g, *Dioscoreae Rhizoma* extract 35 g, *Salviae Miltiorrhizae Radix* ET *Rhizoma* extract 28 g, *Pheretima* extract 7 g, *Rehmanniae Radix* extract 16 g and stir-baked *Atractylodis Macrocephalae Rhizoma* extract 28 g;

The above API extracts are ethanolic extracts obtained by extracting the APIs with 70% ethanol solution via refluxing extraction. The ethanolic API extracts are concentrated, dried by decompressing, mixed well, added with dextrin (as the excipient) according to the ratio of 3:1, blended well, prepared into granules and dried to get the granule preparation.

Embodiment 12

Active pharmaceutical ingredients (APIs): *Astragali Radix* extract 38 g, American *ginseng* extract 11 g, *Cinnamomi Ramulus* extract 14 g, *Angelicae Sinensis Radix* extract 16 g, *Notoginseng Radix* ET *Rhizoma* extract 7 g, *Dioscoreae Rhizoma* extract 28 g, *Salviae Miltiorrhizae Radix* ET *Rhizoma* extract 35 g, *Pheretima* extract 5 g, *Rehmanniae Radix* extract 28 g and stir-baked *Atractylodis Macrocephalae Rhizoma* extract 16 g;

The above API extracts are aqueous extracts obtained by decocting the APIs with water. The aqueous API extracts are concentrated, dried by decompressing and mixed well, then added with dextrin (as the excipient) according to the ratio of 3:1, blended well, prepared into granules and dried to get the granule preparation.

The invention claimed is:

1. A traditional Chinese medicine (TCM) composition for the treatment of diabetic retinopathy, wherein the composition comprises therapeutically effective amounts of extracts of *Astragali radix, Pseudostellariae radix, Cinnamomi Ramulus, Angelica sinensis radix, Notoginseng radix* ET *rhizoma, Dioscoreae rhizoma, Salviae miltiorrhizae radix* ET *rhizoma, Pheretima, Rehmanniae radix*, and *Atractylodis macrocephalae rhizoma*.

2. The TCM composition according to claim 1, wherein the composition comprises the following extracts: *Astragali radix* 10-80 parts by weight, *Pseudostellariae radix* 5-30 parts by weight, *Cinnamomi ramulus* 3-25 parts by weight, *Angelica sinensis radix* 8-60 parts by weight, *Notoginseng radix* ET *rhizoma* 2-15 parts by weight, *Dioscoreae rhizoma* 10-80 parts by weight, *Salviae miltiorrhizae radix* ET *rhizoma* 10-80 parts by weight, *Pheretima* 2-15 parts by weight, *Rehmanniae radix* 8-60 parts by weight, and *Atractylodis macrocephalae rhizoma* 8-60 parts by weight.

3. The TCM composition according to claim 2, wherein the composition comprises the following extracts:
   (a) *Astragali radix* 15-60 parts by weight, *Pseudostellariae radix* 6-25 parts by weight, *Cinnamomi ramulus* 5-20 parts by weight, *Angelica sinensis radix* 10-50 parts by weight, *Notoginseng radix* ET *rhizoma* 3-12 parts by weight, *Dioscoreae rhizoma* 15-60 parts by weight, *Salviae miltiorrhizae radix* ET *Rhizoma* 15-60 parts by weight, *Pheretima* 3-12 parts by weight, *Rehmanniae radix* 10-50 parts by weight, and *Atractylodis macrocephalae Rhizoma* 10-50 parts by weight;
   Or,
   (b) *Astragali radix* 20-50 parts by weight, *Pseudostellariae radix* 8-20 parts by weight, *Cinnamomi ramulus* 8-18 parts by weight, *Angelica sinensis radix* 12-40 parts by weight, *Notoginseng radix* ET *rhizoma* 4-10 parts by weight, *Dioscoreae rhizoma* 20-50 parts by weight, *Salviae miltiorrhizae radix* ET *Rhizoma* 20-50 parts by weight, *Pheretima* 4-10 parts by weight, *Rehmanniae radix* 12-40 parts by weight, and *Atractylodis macrocephalae rhizoma* 12-40 parts by weight;
   Or,
   (c) *Astragali radix* 25-40 parts by weight, *Pseudostellariae radix* 10-18 parts by weight, *Cinnamomi ramulus* 9-15 parts by weight, *Angelica sinensis radix* 15-30 parts by weight, *Notoginseng radix* ET *rhizoma* 5-8 parts by weight, *Dioscoreae rhizoma* 25-40 parts by weight, *Salviae miltiorrhizae radix* ET *Rhizoma* 25-40 parts by weight, *Pheretima* 5-8 parts by weight, *Rehmanniae radix* 15-30 parts by weight, and *Atractylodis macrocephalae rhizoma* 15-30 parts by weight.

4. The TCM composition according to claim 3, wherein the composition comprises the following extracts:
   (a) *Astragali radix* 30 parts by weight, *Pseudostellariae radix* 12 parts by weight, *Cinnamomi ramulus* 10 parts by weight, *Angelica sinensis radix* 20 parts by weight, *Notoginseng radix* ET *rhizoma* 6 parts by weight, *Dioscoreae rhizoma* 30 parts by weight, *Salviae miltiorrhizae radix* ET *Rhizoma* 30 parts by weight, *Pheretima* 6 parts by weight, *Rehmanniae radix* 20 parts by weight, and *Atractylodis macrocephalae Rhizoma* 20 parts by weight;
   Or,
   (b) *Astragali radix* 28 parts by weight, *Pseudostellariae radix* 16 parts by weight, *Cinnamomi ramulus* 9 parts by weight, *Angelica sinensis radix* 28 parts by weight, *Notoginseng radix* ET *rhizoma* 5 parts by weight, *Dioscoreae rhizoma* 35 parts by weight, *Salviae miltiorrhizae radix* ET *Rhizoma* 28 parts by weight, *Pheretima* 7 parts by weight, *Rehmanniae radix* 16 parts by weight, and *Atractylodis macrocephalae Rhizoma* 28 parts by weight;
   Or,
   (c) *Astragali radix* 38 parts by weight, *Pseudostellariae radix* 11 parts by weight, *Cinnamomi ramulus* 14 parts by weight, *Angelica sinensis radix* 16 parts by weight, *Notoginseng radix* ET *rhizoma* 7 parts by weight, *Dioscoreae rhizoma* 28 parts by weight, *Salviae miltiorrhizae radix* ET *Rhizoma* 35 parts by weight, *Pheretima* 5 parts by weight, *Rehmanniae radix* 28 parts by weight, and *Atractylodis macrocephalae Rhizoma* 16 parts by weight.

5. The TCM composition according to claim 2, wherein the *Pseudostellariae Radix* extract can be replaced with *Ginseng radix* ET *rhizoma* extract or *Panacis quinquefolii radix* extract; the *Atractylodis macrocephalae rhizoma* extract is stir-baked; and the *Rehmanniae radix* is unprocessed.

6. A traditional Chinese medicine (TCM) composition for the treatment of diabetic retinopathy, wherein the composition comprises therapeutically effective amounts of *Astragali radix* extract 15-60 parts by weight, *Pseudostellariae radix* extract 6-25 parts by weight, *Cinnamomi ramulus* extract 5-20 parts by weight, *Angelica sinensis radix* extract 10-50 parts by weight, *Notoginseng radix* ET *rhizoma* extract 3-12 parts by weight, *Dioscoreae rhizoma* extract 15-60 parts by weight, *Salviae miltiorrhizae radix* ET *Rhizoma* extract 15-60 parts by weight, *Pheretima* extract 3-12 parts by weight, *Rehmanniae radix* extract 10-50 parts by weight, and *Atractylodis macrocephalae Rhizoma* extract 10-50 parts by weight.

7. A preparation method of a traditional Chinese medicine (TCM) composition for the treatment of diabetic retinopathy or macular edema, wherein the composition comprises therapeutically effective amounts of active pharmaceutical ingredients consisting essentially of extracts of *Astragali radix* 10-80 parts by weight, *Pseudostellariae radix* 5-30 parts by weight, *Cinnamomi ramulus* 3-25 parts by weight, *Angelica sinensis radix* 8-60 parts by weight, *Notoginseng radix* ET *rhizoma* 2-15 parts by weight, *Dioscoreae rhizoma* 10-80 parts by weight, *Salviae miltiorrhizae radix* ET *rhizoma* 10-80 parts by weight, *Pheretima* 2-15 parts by weight, *Rehmanniae radix* 8-60 parts by weight, and *Atractylodis macrocephalae rhizoma* 8-60 parts by weight, the preparation method comprising:
   (i) Taking the active pharmaceutical ingredients each having an amount corresponding to the proportion by weight above, (ii) Extracting the active pharmaceutical ingredients with water or an organic solvent, and Preparing the extracted active pharmaceutical ingredients into an oral dosage form.

8. The preparation method according to claim 7, wherein the oral dosage form comprises granules, tablets, powders, capsules, oral solutions or pills.

\* \* \* \* \*